United States Patent
Good et al.

[11] Patent Number: 5,843,056
[45] Date of Patent: Dec. 1, 1998

[54] ABSORBENT ARTICLE HAVING A COMPOSITE BREATHABLE BACKSHEET

[75] Inventors: Kristeen Elaine Good, Appleton; Allen Todd Leak; Dale Arthur Peterson, both of Neenah; Daniel Robert Schlinz, Greenville, all of Wis.

[73] Assignee: Kimberly-Clark Worldwide, Inc., Neenah, Wis.

[21] Appl. No.: 668,418

[22] Filed: Jun. 21, 1996

[51] Int. Cl.⁶ .................................................. A61F 13/15
[52] U.S. Cl. ............................................................ 604/367
[58] Field of Search ............................................. 604/367

[56] References Cited

U.S. PATENT DOCUMENTS

| | | |
|---|---|---|
| 2,068,997 | 1/1937 | Spanel . |
| 2,068,998 | 1/1937 | Spanel . |
| 2,544,069 | 3/1951 | Cutler . |
| 2,604,097 | 7/1952 | White . |
| 2,649,859 | 8/1953 | Hermanson et al. . |

(List continued on next page.)

FOREIGN PATENT DOCUMENTS

| | | |
|---|---|---|
| 1 146 298 | 5/1983 | Canada . |
| 1 182 603 | 2/1985 | Canada . |
| 1 189 252 | 6/1985 | Canada . |
| 1 204 557 | 5/1986 | Canada . |
| 1 222 103 | 5/1987 | Canada . |
| 1 252 952 | 4/1989 | Canada . |
| 1 255 577 | 6/1989 | Canada . |
| 2023038 | 2/1991 | Canada . |
| 2008440 | 3/1991 | Canada . |
| 1 285 129 | 6/1991 | Canada . |
| 2024472 | 6/1991 | Canada . |
| 1291326 | 10/1991 | Canada . |
| 1311181 | 12/1992 | Canada . |
| 1312426 | 1/1993 | Canada . |
| 2088218 | 7/1993 | Canada . |
| 2068491 | 11/1993 | Canada . |
| 2116081 | 6/1995 | Canada . |
| 0 104 906 B1 | 4/1984 | European Pat. Off. . |
| 0 360 929 A1 | 4/1990 | European Pat. Off. . |
| 0 457 905 B1 | 11/1991 | European Pat. Off. . |
| 0 710 472 A1 | 5/1995 | European Pat. Off. . |
| 0705584A1 | 4/1996 | European Pat. Off. . |
| 0 710 471 A1 | 5/1996 | European Pat. Off. . |
| 3 343 622 A1 | 6/1985 | Germany . |
| 2241871 | 9/1991 | United Kingdom . |
| 2264258 | 8/1993 | United Kingdom . |
| 2 290 052 | 12/1995 | United Kingdom . |
| 94/23107 | 10/1994 | WIPO . |
| 94/23947 | 10/1994 | WIPO . |
| 95/25496 | 9/1995 | WIPO . |
| 96/09165 | 3/1996 | WIPO . |
| WO 96/14034 A1 | 5/1996 | WIPO . |
| WO 96/14037 A1 | 5/1996 | WIPO . |
| WO 96/14038 | 5/1996 | WIPO . |
| WO 96/16562 A1 | 6/1996 | WIPO . |

*Primary Examiner*—Mark O. Polutta
*Attorney, Agent, or Firm*—Jeffrey B. Curtin

[57] ABSTRACT

An absorbent article includes a substantially liquid impermeable, vapor permeable composite backsheet, a liquid-permeable topsheet positioned in facing relation with the backsheet and an absorbent body located between the backsheet and topsheet. The composite backsheet includes a polymeric film of relatively low basis weight and a nonwoven facing layer which enhances the strength of the composite backsheet and a provides a clothlike feel to the composite backsheet.

47 Claims, 1 Drawing Sheet

U.S. PATENT DOCUMENTS

| | | | |
|---|---|---|---|
| 2,664,895 | 1/1954 | Shulman . | |
| 2,675,805 | 4/1954 | Trimble . | |
| 2,896,626 | 7/1959 | Voigtman . | |
| 2,897,108 | 7/1959 | Harwood . | |
| 2,897,109 | 7/1959 | Voigtman . | |
| 2,964,040 | 12/1960 | Ashton et al. . | |
| 3,004,895 | 10/1961 | Schwartz . | |
| 3,156,242 | 11/1964 | Crowe, Jr. . | |
| 3,315,676 | 4/1967 | Cooper . | |
| 3,402,715 | 9/1968 | Liloia et al. . | |
| 3,426,754 | 2/1969 | Bierenbaum et al. . | |
| 3,463,154 | 8/1969 | Hendricks . | |
| 3,559,649 | 2/1971 | Grad et al. . | |
| 3,559,650 | 2/1971 | Larson . | |
| 3,570,491 | 3/1971 | Sneider . | |
| 3,676,242 | 7/1972 | Prentice . | |
| 3,695,967 | 10/1972 | Ross . | |
| 3,779,246 | 12/1973 | Mesek et al. . | |
| 3,881,489 | 5/1975 | Hartwell . | |
| 3,882,871 | 5/1975 | Taniguchi . | |
| 3,903,889 | 9/1975 | Torr . | |
| 3,911,186 | 10/1975 | Trotman . | |
| 3,932,682 | 1/1976 | Loft et al. . | |
| 3,989,867 | 11/1976 | Sisson . | |
| 4,015,604 | 4/1977 | Csillag . | |
| 4,059,114 | 11/1977 | Richards . | |
| 4,138,459 | 2/1979 | Brazinsky et al. . | |
| 4,196,245 | 4/1980 | Kitson et al. . | |
| 4,241,462 | 12/1980 | Tagawa et al. . | |
| 4,289,832 | 9/1981 | Schwarz . | |
| 4,306,559 | 12/1981 | Nishizawa et al. . | |
| 4,333,463 | 6/1982 | Holtman . | |
| 4,338,371 | 7/1982 | Dawn et al. . | |
| 4,341,216 | 7/1982 | Obenour . | |
| 4,376,147 | 3/1983 | Byrne et al. . | |
| 4,379,192 | 4/1983 | Wahlquist et al. . | |
| 4,384,024 | 5/1983 | Mitchell et al. . | |
| 4,411,660 | 10/1983 | Dawn et al. . | |
| 4,427,408 | 1/1984 | Karami et al. . | |
| 4,480,000 | 10/1984 | Watanabe et al. . | |
| 4,522,203 | 6/1985 | Mays . | |
| 4,522,874 | 6/1985 | Pommez . | |
| 4,546,029 | 10/1985 | Cancio et al. . | |
| 4,578,066 | 3/1986 | O'Connor | 604/366 |
| 4,606,970 | 8/1986 | Sharps, Jr. . | |
| 4,609,584 | 9/1986 | Cutler et al. . | |
| 4,610,681 | 9/1986 | Strohbeen et al. | 604/396 |
| 4,623,340 | 11/1986 | Luceri . | |
| 4,626,252 | 12/1986 | Nishizawa et al. | 604/370 |
| 4,627,847 | 12/1986 | Puletti et al. | 604/366 |
| 4,632,860 | 12/1986 | D'Antonio et al. . | |
| 4,636,207 | 1/1987 | Buell | 604/370 |
| 4,639,949 | 2/1987 | Ales et al. | 2/400 |
| 4,648,876 | 3/1987 | Becker et al. | 604/370 |
| 4,662,875 | 5/1987 | Hirotsu et al. | 604/389 |
| 4,681,578 | 7/1987 | Anderson et al. . | |
| 4,681,793 | 7/1987 | Linman et al. . | |
| 4,692,161 | 9/1987 | Puletti et al. | 604/366 |
| 4,713,068 | 12/1987 | Wang et al. | 604/366 |
| 4,713,069 | 12/1987 | Wang et al. | 604/378 |
| 4,718,898 | 1/1988 | Puletti et al. | 604/366 |
| 4,725,473 | 2/1988 | Van Gompel et al. . | |
| 4,734,324 | 3/1988 | Hill . | |
| 4,758,239 | 7/1988 | Yeo et al. | 604/366 |
| 4,777,073 | 10/1988 | Sheth . | |
| 4,798,602 | 1/1989 | Laus | 604/372 |
| 4,798,603 | 1/1989 | Meyer et al. | 604/378 |
| 4,818,600 | 4/1989 | Braun et al. . | |
| 4,822,350 | 4/1989 | Ito et al. | 604/372 |
| 4,822,435 | 4/1989 | Igaue et al. . | |
| 4,824,718 | 4/1989 | Hwang | 428/284 |
| 4,828,556 | 5/1989 | Braun et al. | 604/365 |
| 4,851,470 | 7/1989 | George . | |
| 4,883,480 | 11/1989 | Huffman et al. | 604/385.1 |
| 4,887,602 | 12/1989 | O'Leary | 604/305.1 |
| 4,902,553 | 2/1990 | Hwang et al. . | |
| 4,929,303 | 5/1990 | Sheth . | |
| 4,935,021 | 6/1990 | Huffman et al. | 604/385.1 |
| 5,026,591 | 6/1991 | Henn et al. . | |
| 5,062,839 | 11/1991 | Anderson | 604/385.1 |
| 5,069,678 | 12/1991 | Yamamoto et al. | 604/385.1 |
| 5,085,654 | 2/1992 | Buell | 604/370 |
| 5,098,423 | 3/1992 | Pieniak et al. | 604/385.1 |
| 5,114,418 | 5/1992 | Levy | 604/365 |
| 5,169,712 | 12/1992 | Tapp . | |
| 5,171,239 | 12/1992 | Igaue et al. | 604/385.2 |
| 5,176,668 | 1/1993 | Bernardin | 604/368 |
| 5,176,672 | 1/1993 | Bruemmer et al. | 604/385.1 |
| 5,188,626 | 2/1993 | Toyoda et al. | 604/385.1 |
| 5,192,606 | 3/1993 | Proxmire et al. | 428/284 |
| 5,208,098 | 5/1993 | Stover . | |
| 5,223,311 | 6/1993 | Tsutsumi et al. . | |
| 5,263,948 | 11/1993 | Karami et al. | 604/383 |
| 5,263,949 | 11/1993 | Karami et al. | 604/383 |
| 5,292,316 | 3/1994 | Suzuki | 604/385.2 |
| 5,342,469 | 8/1994 | Bodford et al. . | |
| 5,364,381 | 11/1994 | Soga et al. | 604/366 |
| 5,385,972 | 1/1995 | Yamamoto et al. . | |
| 5,409,761 | 4/1995 | Langley . | |
| 5,451,467 | 9/1995 | Lock . | |
| 5,498,463 | 3/1996 | McDowall et al. . | |
| 5,507,736 | 4/1996 | Clear et al. | 604/385.2 |
| 5,509,915 | 4/1996 | Hanson et al. | 604/378 |
| 5,523,146 | 6/1996 | Bodford et al. | 428/198 |
| 5,560,974 | 10/1996 | Langley | 428/198 |
| 5,571,096 | 11/1996 | Dobrin et al. | 604/383 |

ABSORBENT ARTICLE HAVING A COMPOSITE BREATHABLE BACKSHEET

BACKGROUND OF THE INVENTION

1. Field of the Invention

The present invention relates to an absorbent article for absorbing body fluids and exudates, such as urine and fecal material. More particularly, the present invention relates to backsheets or outer covers for absorbent garments, such as disposable diapers and adult incontinence garments, which are liquid impermeable and vapor permeable.

2. Description of the Related Art

Conventional absorbent articles, such as disposable diapers, employ absorbent materials located between a liquid pervious topsheet and a liquid impermeable backsheet to absorb body exudates. Such conventional absorbent articles have typically included elasticized waistbands and leg cuffs to help reduce the leakage of body exudates. Some conventional absorbent articles have also included elasticized containment or barrier flaps at the leg or waist sections of the article to further reduce leaks.

The liquid impermeable backsheet on conventional absorbent articles is configured to provide a barrier between the absorbent body within the absorbent article and the wearer's clothes. Typical backsheets have been both liquid and vapor impermeable. For example, many conventional absorbent articles have included a backsheet made from a polymeric film which is both liquid and vapor impermeable. To provide such backsheets with a more clothlike feel, facing layers of nonwoven materials have been added to the polymeric film layer to provide a more pleasing feel. Unfortunately, the use of liquid and vapor impermeable backsheets can result in a relatively high degree of humidity within the diaper when in use. This may result in relatively high skin hydration levels which have led to the onset of diaper rash.

In an effort to reduce the level of humidity within the diaper and the level of skin hydration of the wearer, the backsheets on some conventional absorbent articles have been rendered vapor permeable. For example, some conventional absorbent articles have included backsheets constructed of a polymeric film which has been perforated. Other conventional absorbent articles have included single layer or composite nonwoven layers which have been treated to be liquid impermeable. Still other conventional absorbent articles have included polymeric films which have fractures therein to provide vapor permeability. Such films have been formed by adding fillers, such as calcium carbonate, when making the film and then stretching the film to provide the fractures where the filler is located. Still other conventional absorbent articles have been designed to have specific areas or panels on the backsheets which have been vapor permeable to help ventilate the article.

However, conventional absorbent articles which incorporate such breathable backsheets have not been completely satisfactory. For example, polymeric films which have been perforated typically allow very high levels of humidity to pass through which has undesirably resulted in a damp clammy feeling on the outer surface of the film. Such films also do not have a clothlike feeling and may be rather stiff and noisy in use. The perforated films have also allowed excessive levels of leakage of liquids which can excessively soil the wearer's clothes. Although, backsheets which have included nonwoven materials or laminates of several nonwoven layers have been vapor permeable, such backsheets have not exhibited the desired level of liquid impermeability which has also undesirably resulted in soiling of the wearer's clothes. Moreover, films which have included fillers and which have been stretched to provide fractures for vapor permeability have been very expensive to manufacture and typically do not have very high strength. As a result, the fractures in such backsheets have split open further when the wearer exerts pressure and forces upon the backsheet during use. Such films also do not have the desired clothlike feeling for such backsheets.

As a result, conventional absorbent articles having breathable backsheets have not been able to sufficiently reduce the hydration of the wearer's skin while providing the desired level of liquid impermeability. Accordingly, there remains a need to provide low cost, high strength, clothlike backsheets for absorbent articles which are both liquid impermeable and vapor permeable to reduce the level of skin hydration and the occurrence of rash on the skin of the wearer.

SUMMARY OF THE INVENTION

In response to the difficulties and problems discussed above, a new disposable absorbent article which has an improved breathable backsheet has been discovered.

As used herein, a liquid impermeable material is constructed to provide a hydrohead of at least about 50 centimeters, desirably at least about 75 centimeters, and more desirably at least about 90 centimeters. A suitable technique for determining the hydrohead value is the Hydrostatic Pressure Test which is described in further detail herein below.

As used herein, a vapor permeable material is constructed to provide a water vapor transmission rate (WVTR) of at least about 100 g/sq. m/24 hr. A suitable technique for determining the WVTR value is the WVTR Test which is described in further detail herein below.

In one aspect, the present invention relates to an absorbent article which includes a substantially liquid impermeable, vapor permeable composite backsheet which comprises a substantially liquid impermeable, vapor permeable film which defines a basis weight of less than about 20.0 grams per square meter and a nonwoven facing layer which is attached to a garment facing surface of the film and which defines a strength in a machine direction of at least about 3000 grams at an elongation of 30 percent. In a particular embodiment, the ratio of the strength of the composite backsheet to a strength of the film in the machine direction at an elongation of 30 percent is at least about 2:1. The composite backsheet defines a water vapor transmission rate of at least about 500 g/sq. m/24 hr.

In another aspect, the present invention relates to an absorbent article which comprises a substantially liquid impermeable composite backsheet which includes a polymeric film which defines a basis weight of less than about 20.0 grams per square meter and a nonwoven facing layer attached to a garment facing surface of the film. The composite backsheet defines a water vapor transmission rate of at least about 500 g/sq.m/24 hr and a hydrohead value of at least about 50 centimeters. The article further comprises a liquid permeable topsheet which is positioned in facing relation with the backsheet and an absorbent body located between the backsheet and the topsheet. In a particular embodiment, the film substantially covers a garment side of the absorbent body.

In yet another aspect, the present invention relates to an absorbent article which includes a substantially liquid impermeable, vapor permeable composite backsheet which comprises a substantially liquid impermeable, vapor permeable polyethylene film which includes at least about 20 weight percent filler particles and which defines a basis weight of less than about 20.0 grams per square meter and a meltblown facing layer which is attached to a garment facing surface of the film and which defines basis weight of less than about 30.0 grams per square meter and a hydrohead value of at least about 50 centimeters. A ratio of the strength of the composite backsheet to a strength of the film in the machine direction at an elongation of 30 percent is at least about 2:1. In a particular embodiment, the composite backsheet defines a strength of at least about 3500 grams at an elongation of 30 percent.

The various aspects of the present invention can advantageously provide an absorbent article which provides the wearer with a reduced level of skin hydration during use. Thus, wearer's of absorbent articles made according to the present invention should have a reduced incidence of skin irritation or rash.

BRIEF DESCRIPTION OF THE DRAWINGS

The invention will be more fully understood and further advantages will become apparent when reference is made to the following detailed description of the invention and the accompanying drawing, in which.

DETAILED DESCRIPTION OF THE INVENTION

Figure 1:
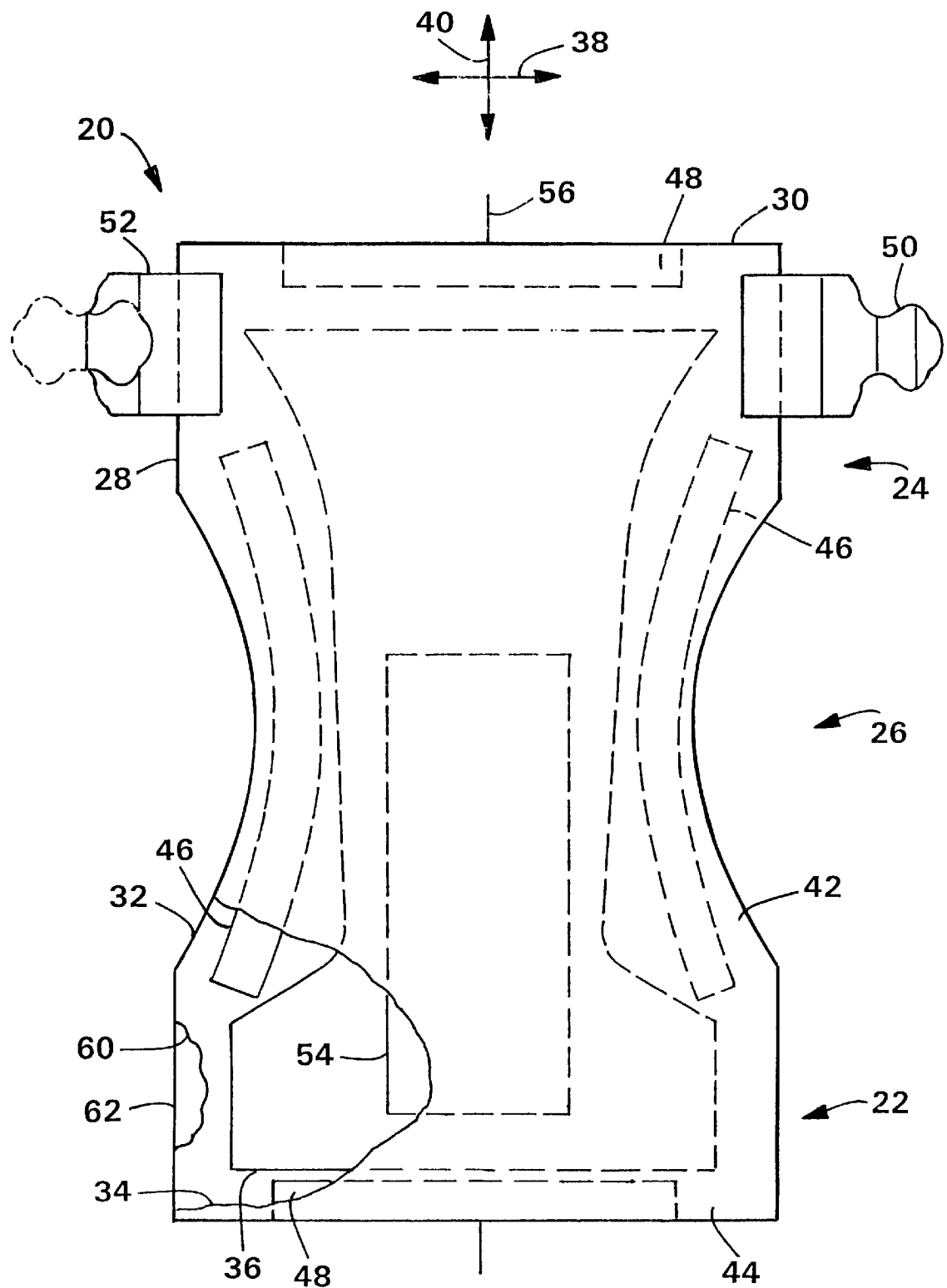
FIG. 1 representatively shows a partially cut away, top plan view of an absorbent article according to one embodiment of the invention.

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like. In addition, the invention will be described in the context of its various configurations. It should be appreciated that alternative arrangements of the invention can comprise any combination of such configurations.

With reference to FIG. 1, an integral absorbent garment article, such as the disposable diaper 20, generally defines a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

FIG. 1 is a representative plan view of the diaper 20 of the present invention in a flat, uncontracted state. Portions of the structure are partially cut away to more clearly show the interior construction of the diaper 20, and the surface of the diaper which contacts the wearer is facing the viewer. The diaper 20 includes a substantially liquid impermeable, vapor permeable, composite backsheet 32, a porous, liquid permeable topsheet 34 positioned in facing relation with the backsheet 32, and an absorbent body 36, such as an absorbent pad, which is located between the backsheet and the topsheet. The diaper 20 also defines a lateral direction 38 and a longitudinal direction 40. Marginal portions of the diaper 20, such as marginal sections of the backsheet 32, may extend past the terminal edges of the absorbent body 36. In the illustrated embodiment, for example, the backsheet 32 extends outwardly beyond the terminal marginal edges of the absorbent body 36 to form side margins 42 and end margins 44 of the diaper 20. The topsheet 34 is generally coextensive with the backsheet 32 but may optionally cover an area which is larger or smaller than the area of the backsheet 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics are configured to operably gather and shirr the waistband sections to provide a resilient, comfortably close fit around the waist of the wearer.

The elastic members 46 and 48 are secured to the diaper 20 in an elastically contractible condition so that in a normal under strain configuration, the elastic members effectively contract against the diaper 20. For example, the elastic members 46 and 48 may be elongated and secured to the diaper 20 while the diaper is in an uncontracted condition. In FIG. 1, the elastic members 46 and 48 are illustrated in their uncontracted, stretched condition for the purpose of clarity. Alternatively, the diaper 20 may include a pair of separate, elasticized and gathered leg gussets (not shown) which are attached to the diaper along the side margins 42 in at least the intermediate section 26 of the diaper 20 to provide elasticized leg cuffs. Such leg gussets may be configured to extend beyond and bridge across the respective concave portion of the side margins 42.

The diaper 20, as representatively illustrated in FIG. 1, may further include a pair of fasteners 50 which are employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member can be associated with each fastener and may be constructed to be nonelasticized, or to be elastically stretchable at least along the lateral direction 38 of the diaper 20.

The diaper 20 may also include a pair of elasticized, longitudinally extending containment flaps (not shown) which are configured to maintain an upright, perpendicular arrangement in at least the intermediate section 26 of the diaper 20 to serve as an additional barrier to the lateral flow of body exudates. The diaper 20 may further include a surge management layer (not shown) positioned between the topsheet 34 and the absorbent body 36 which is configured to efficiently hold and distribute liquid exudates to the absorbent body 36. The surge management layer can prevent the liquid exudates from pooling and collecting on the portion of the diaper positioned against the wearer's skin, thereby reducing the level of skin hydration. Suitable constructions and arrangements of containment flaps and surge management layers are well known to those skilled in the art. Other suitable diaper components may also be incorporated on absorbent articles of the present invention.

The diaper 20 may be of various suitable shapes. For example, the diaper may have an overall rectangular shape, T-shape or an approximately hour-glass shape. In the shown embodiment, the diaper 20 has a generally I-shape. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bemardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference to the extent they are consistent herewith. The various aspects and configurations of the invention can provide distinctive combinations of softness, body conformity, reduced red-marking of the wearers skin, reduced skin hydration, and improved containment of body exudates.

The various components of the diaper 20 are integrally assembled together employing various types of suitable attachment means, such as adhesive, sonic bonds, thermal bonds or combinations thereof. In the shown embodiment, for example, the topsheet 34 and composite backsheet 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 46 and 48 and the fasteners 50, may be assembled into the diaper 20 article by employing the above-identified attachment mechanisms.

The topsheet 34, as representatively illustrated in FIG. 1, suitably presents a bodyfacing surface which is compliant, soft feeling, and nonirritating to the wearer's skin. Further, the topsheet 34 may be less hydrophilic than the absorbent body 36, to present a relatively dry surface to the wearer, and may be sufficiently porous to be liquid permeable, permitting liquid to readily penetrate through its thickness. A suitable topsheet 34 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet 34 is suitably employed to help isolate the wearers skin from liquids held in the absorbent body 36.

Various woven and nonwoven fabrics can be used for the topsheet 34. For example, the topsheet may be composed of a meltblown or spunbonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. In a particular embodiment of the present invention, the topsheet 34 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.28 weight percent of a surfactant commercially available from the Rohm and Haas Co. under the trade designation TRITON X-102. The surfactant may be applied by any conventional means, such as spraying, printing, brush coating or the like. The surfactant may be applied to the entire topsheet 34 or may be selectively applied to particular sections of the topsheet 34, such as the medial section along the longitudinal centerline of the diaper, to provide greater wettability of such sections.

The absorbent body 36 of the diaper 20, as representatively illustrated in FIG. 1, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 36.

Optionally, a substantially hydrophilic tissue wrapsheet (not illustrated) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass. The composite backsheet 32 of the diaper 20, as representatively illustrated in FIG. 1, includes a substantially liquid impermeable, vapor permeable film 60 which is attached to a nonwoven facing layer 62. The film 60 is configured to allow vapor to escape from the absorbent article while preventing any liquid exudates from passing through the absorbent body 36 to the wearers clothes. The nonwoven facing layer 62 is configured to reinforce the film 60 to increase it's resistance to rips and tears as a result of the forces exerted by the wearer upon the diaper 20. The nonwoven facing layer 62 also prevents liquids from striking through the composite backsheet 32 as a result of a pin hole or other enlarged aperture in the film 60. The nonwoven facing layer 62 is further configured to provide a soft, clothlike surface on the garment side of the diaper 20. The film 60 is positioned in facing relation with the absorbent body 36 and the nonwoven facing layer 62 is positioned in facing relation with the film 60.

The film 60 and nonwoven facing layer 62 of the composite backsheet 32 may be attached to each other using conventional techniques known to those skilled in the art such as adhesive, thermal or ultrasonic bonding techniques. The film and nonwoven facing layer may be attached over their entire mating surface or only a portion thereof. For example, in a particular embodiment the film 60 may be adhesively attached to the nonwoven facing layer 62 intermittently across the width of the composite backsheet 32 or around the outer edges of the composite backsheet 32 in a windowpane configuration.

Films which have been rendered vapor permeable are well known to those skilled in the art. However, to provide sufficient strength and liquid impermeability, the basis weight of such films has been relatively high which undesirably results in higher cost and less flexibility of the film. Such high costs have made it difficult to incorporate such films in disposable articles such as diapers. However, Applicants have discovered that the basis weight of the film 60 of the present invention can be reduced to weights which are much more cost effective for disposable type products by using the nonwoven facing layer 62 to enhance the strength and liquid impermeability of the film. The low basis weight films are also much more flexible which provides improved fit and performance of the article. For example, the film 60 of the composite backsheet 32 of the present invention may define a basis weight of less than about 20.0 grams per square meter, desirably less than about 15.0 grams per square meter, and more desirably less than about 12.0 grams per square meter.

At the relatively low basis weights set forth above, the film 60 of the present invention has a relatively low strength and is not capable of elongating a great amount before rupture. Typically, such films define a strength in the machine direction of less than about 2000 grams at an elongation of 30 percent. As used herein, the term "machine direction" refers to the direction in which the material, such as the film, is manufactured. Such low strength is not particularly desirable for performance but provides a more cost effective film for disposable articles. By themselves, such films do not have sufficient strength to withstand the forces exerted upon the backsheet 32 by the wearer. However, the nonwoven facing layer 62 of the backsheet 32 of the present invention enhances the strength and liquid impermeability of such films to provide improved performance without adding an excessive cost to the backsheet 32.

The film 60 of the composite backsheet 32 of the diaper 20, as representatively illustrated in FIG. 1, is configured to be substantially liquid impermeable. In a particular embodiment, the film 60 defines a hydrohead value of at least about 50 cm, desirably at least about 70 cm, and more desirably at least about 90 centimeters when subjected to the Hydrostatic Pressure Test. Hydrohead values less than those above undesirably result in the strike through of liquids, such as urine, during use. The film 60 is further constructed to be substantially permeable to at least water vapor and defines a water vapor transmission rate of at least about 500 g/sq.m/24 hr., desirably from about 1000 to about 5000 g/sq.m/24 hr, and more desirably from about 1000 to about 2500 g/sq.m/24 hr. Applicants have discovered that when the film 60 defines water vapor transmission rates less than those above, the composite backsheet 32 does not allow sufficient transfer of vapor which undesirably results in high levels of skin hydration and rash. Water vapor transmission rates greater than those above result in excessive condensation of vapor on the garment facing surface of the backsheet 32 which undesirably results in a damp feeling.

The film 60 of the composite backsheet 32 may suitably be composed of a material which provides the desired levels of liquid impermeability, vapor permeability, low basis weight (low cost), and a relatively high strength at such low basis weights. For example, the film may be selected from polyolefin films, such as a polyethylene or polypropylene film. Applicants have discovered that, at the desired low basis weights, polyethylene films are particularly desirably due to their relatively high level of strength. For example, the film 60 of the composite backsheet 32 of the present invention may be formed from a polyethylene film having a thickness of less than about 0.025 millimeters (1 mil) and desirably from about 0.008 millimeters (0.3 mils) to about 0.018 millimeters (0.7 mils). Desirably, the film 60 has been stretch-thinned to provide a more cost effective layer for use in disposable articles. Such films are typically vapor impermeable but may be rendered vapor permeable by perforating the film to provide small fractures or apertures which allow vapor but not liquids to pass through.

In a particular embodiment, the film 60 may be rendered vapor permeable by adding filler particles to the film composition and subsequently stretching the film to cause fractures to form where the filler particle are located. For example, the film 60 may include filler particles such as calcium carbonate. After the film is formed by methods known to those skilled in the art, it is stretched to thin the material and cause fractures to form where the filler particles are located which renders the film vapor permeable. Such stretching is controlled such that the fractures are not so large that they would allow liquids to pass through. It is also desirable that such films have been biaxially oriented by methods known to those skilled in the art to improve the strength and tear resistance of the film.

The filler particles added to such films typically range in size from about 1 to about 10 microns. The amount of filler particles added to the film depends upon the desired properties of the film such as the water vapor transmission rate, tear resistance, and stretchability. To provide the levels of water vapor transmission desired in the present invention, such films may include at least about 20 weight percent, desirably at least about 30 weight percent, and more desirably at least about 40 weight percent filler particles. To provide the desired levels of vapor permeability to such films, the films are stretched in the machine direction, transverse direction (perpendicular to the machine direction) or biaxially in both the machine direction and the transverse direction at least about 150 percent, desirably at least about 200 percent, and more desirably at least about 300 percent. Desirably, the films are biaxially stretched to provide improved breathability and strength. Applicants have discovered that films having such high levels of filler particles, high levels of stretching and the low basis weights described above are particularly low in strength compared to low basis weight films which do not include such filler particles and which have not been stretched to such a degree.

A particularly desirable material for use as the film 60 of the present invention is a biaxially oriented polyethylene film material which includes about 50 weight percent calcium carbonate and which is commercially available from Exxon Chemical Patents, Incorporated, a business having offices located in Linden, N.J. under the trade designation EXXAIRE.

The film 60 of the composite backsheet 32 of the different aspects of the present invention, effectively prevents the transfer of liquids while allowing sufficient vapor to pass through the composite backsheet 32 to reduce the level of skin hydration of the wearer. The film 60 may also prevent the transfer of excessive vapor or a high level of humidity from the interior of the diaper 20. In many instances this is desirable since a high degree of transfer of humidity across the entire surface of the diaper has been found to produce a clammy feeling on the outer surface of the diaper which many consumers perceive in a negative manner.

The nonwoven facing layer 62 of the composite backsheet 32 of the present invention is configured to enhance the strength of the low basis weight film 60 such that it does not rupture thereby undesirably allowing leakage of liquids from the diaper 20. Applicants have discovered that the basis weight of the nonwoven facing layer 62 of the present invention can be relatively low while still having the ability to enhance the strength and liquid impermeability of the film 60. For example, the nonwoven facing layer 62 of the composite backsheet 32 of the present invention may define a basis weight of less than about 30.0 grams per square meter, desirably less than about 25.0 grams per square meter, and more desirably less than about 20.0 grams per square meter.

At the relatively low basis weights set forth above, the nonwoven facing layer 62 of the present invention has sufficient strength to assist the film 60 while not being cost ineffective. Typically, facing layers which are suitable for the present invention define a strength in the machine direction of at least about 3000 grams and desirably at least about 4000 grams at an elongation of about 30 percent. The combination of the film 60 and the nonwoven facing layer 62 to provide the composite backsheet 32 of the present invention strengthens the backsheet to avoid rupture without adding an excessive cost to the backsheet 32.

The nonwoven facing layer 62 of the backsheet 32 of the diaper 20, as representatively illustrated in FIG. 1, is configured to have some level of liquid impermeability to help prevent any liquids from passing through the polymeric film 60 if the film develops a pin hole or enlarged aperture. In a particular embodiment, the nonwoven facing layer 62 defines a hydrohead value of at least about 50 cm, desirably at least about 70 cm, and more desirably at least about 90 centimeters when subjected to the Hydrostatic Pressure Test. Hydrohead values less than those above undesirably result in the strike through of liquids, such as urine, during use. The nonwoven facing layer 62 is further constructed to be substantially permeable to at least water vapor and defines a water vapor transmission rate of at least about 2500 g/sq.m/24 hr., desirably from about 2500 to about 6000 g/sq.m/24 hr, and more desirably from about 4000 to about 5000 g/sq.m/24 hr.

The nonwoven facing layer 62 of the composite backsheet 32 of the present invention may be any type of nonwoven which provides the desired strength to the backsheet and increased level of liquid impermeability. The nonwoven facing layer 62, as representatively illustrated in FIG. 1, suitably presents a bodyfacing surface which is compliant, soft feeling, and nonirritating to the wearer's skin. Various nonwoven materials can be used for the facing layer 62. For example, the facing layer 62 may be composed of a meltblown or spunbonded web of polyolefin fibers. The facing layer 62 may also be a bonded-carded web composed of natural and/or synthetic fibers. The facing layer 62 may be composed of a substantially hydrophobic material, and the hydrophobic material may, optionally, be treated to impart a desired level of liquid impermeability.

In a particular embodiment of the present invention, the nonwoven facing layer 62 comprises at least one meltblown layer for improved strength. For example, the nonwoven facing layer 62 may include a spunbond/meltblown material or a spunbond/meltblown/spunbond material which are formed by conventional spunbond and meltblown technology. Desirably, the meltblown layer comprises polypropylene and the spunbond layers comprise polyethylene/polypropylene fibers which define a fiber denier of about 2 to about 10.

The combination of the substantially liquid impermeable, vapor permeable film 60 with the nonwoven facing layer 62 to provide the composite backsheet 32 of the absorbent article, as representatively illustrated in FIG. 1, is configured to enhance the breathability of the article to reduce the hydration of the wearer's skin during use. The film 60 is designed to provide the maximum humidity transfer from the absorbent article without excessive condensation of vapor on the garment facing surface of the backsheet while the nonwoven facing layer 62 is designed to provide strength to the film 60 and a clothlike feeling to the garment facing surface of the composite backsheet 32.

The nonwoven facing layer 62 generally extends beyond the edges of the absorbent body 36 to the outermost edges of the diaper 20. In the illustrated embodiment, the film 60 is coextensive with the nonwoven facing layer 62. However, it should be recognized that the film 60 may define a smaller shape and size than the facing layer 62. For example, the film 60 may have any desired configuration which prevents liquids from passing through the backsheet 32 including rectangular, hourglass, oval, and the like. The film 60 may have any desired dimensions which effectively provides improved humidity transfer while preventing excessive condensation of vapor from the absorbent body 36 through and onto the garment facing surface of the backsheet 32. It is desirable that the film 60 cover at least the garment facing surface of the absorbent body 36 of the diaper 20 for improved performance. In a particular embodiment, it is desirable that the film 60 define an area which is at least about 70 percent and desirably at least about 90 percent of the area of the nonwoven facing layer 62. When the area of the film 60 is too small, the diaper 20 may exhibit an undesirable amount of leakage or condensation of vapor on the exposed, garment facing surface of the backsheet 32 resulting in a clammy feeling on the outer surface of the diaper.

The composite backsheet 32 of the diaper 20, as representatively illustrated in FIG. 1, is configured to be substantially liquid impermeable and vapor permeable. In a particular embodiment, the composite backsheet 32 defines a hydrohead value of at least about 50 cm, desirably at least about 70 cm, and more desirably at least about 90 centimeters when subjected to the Hydrostatic Pressure Test. Hydrohead values less than those above undesirably result in the strike through of liquids, such as urine, during use. The composite backsheet 32 is further constructed to be substantially permeable to at least water vapor and defines a water vapor transmission rate of at least about 500 g/sq.m/24 hr., desirably from about 1000 to about 3000 g/sq.m/24 hr, and more desirably from about 1200 to about 2000 g/sq.m/24 hr. Applicants have discovered that when the composite backsheet 32 defines water vapor transmission rates less than those above, the backsheet 32 does not allow sufficient transfer of vapor which undesirably results in high levels of skin hydration and rash. Water vapor transmission rates greater than those above result in excessive condensation of vapor on the garment facing surface of the backsheet 32 which undesirably results in a damp feeling.

The composite backsheet 32 of the present invention is further configured to provide sufficient strength to resist breaks or tears during use. For example, the composite backsheet 32 may define a strength in the machine direction of at least about 3500 grams, desirably at least about 4500 grams, and more desirably at least about 5000 grams at an elongation of 30 percent. Applicants have discovered that when the composite backsheet 32 defines strengths less than those above, the backsheet 32 may rupture during use undesirably resulting in leakage during use. The composite backsheet 32 of the present invention may also define a basis weight of less than about 60.0 grams per square meter, desirably less than about 50.0 grams per square meter, and more desirably less than about 45.0 grams per square meter for improved cost effectiveness.

As set forth above, the nonwoven facing layer 62 of the composite backsheet 32 is configured to enhance both the liquid impermeability and the strength of the low basis weight film 60. In a particular embodiment, a ratio of the strength of the composite backsheet 32 to the strength of the film 60 in the machine direction at an elongation of 30 percent is at least about 2:1, desirably at least about 3:1, and more desirably at least about 4:1 for improved performance.

As a result, Applicants have discovered a new composite backsheet for use in disposable absorbent articles which combines a low basis weight, substantially liquid impermeable, vapor permeable film with a nonwoven facing layer to provide a breathable, strong, and cost effective backsheet.

TEST PROCEDURES

Hydrostatic Pressure Test

The Hydrostatic Pressure Test is a measure of the liquid barrier properties of a material. In general, the Hydrostatic Pressure Test determines the height of water (in centimeters) in a column which the material will support before a predetermined amount of water passes through. A material with a higher hydrohead value indicates it is a greater barrier to liquid penetration than a material having a lower hydrohead value. The Hydrostatic Pressure Test is performed according to Method 5514—Federal Test Methods Standard No. 191A.

Water Vapor Transmission Rate Test

A suitable technique for determining the WVTR (water vapor transmission rate) value of is a material is as follows. For the purposes of the present invention, 3-inch diameter (76 millimeter) circular samples are cut from the test material and from a control material, CELGUARD™ 2500 (Hoechst Celanese Corporation). Two or three samples are prepared for each material. Test cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred milliliters of distilled water are poured into each Vapometer cup, and each of the individual samples of the test materials and control material are placed across the open top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.). The oven is a constant temperature oven with external air circulating through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary, test WVTR value is calculated as follows:

$$\text{Test } WVTR = \frac{[(\text{grams weight loss over 24 hours}) \times 7571]}{24} \; (g/m^2/24 \text{hours})$$

The relative humidity within the oven is not specifically controlled. Under predetermined set conditions of 100° F. and ambient relative humidity, the WVTR for CELGUARD 2500 has been determined to be 5000 g/m$^2$/24 hours. Accordingly, CELGUARD 2500 is run as a control sample with each test. CELGUARD 2500 is a 0.0025 cm thick film composed of a microporous polypropylene.

The following examples are presented to provide a more detailed understanding of the invention. The specific materials and parameters are exemplary and are not intended to specifically limit the scope of the invention.

EXAMPLE 1

Material which could be used as the composite backsheet on absorbent articles such as diapers was produced according to the present invention. The liquid impermeable, vapor permeable composite backsheet 32 comprised a low density polyethylene film material having a basis weight of 19.5 grams per square meter which was adhesively attached to a spunbond/meltblown/spunbond (SMS) laminate material having a basis weight of 27 grams per square meter.

The film comprised a biaxially oriented polyethylene film material which included about 50 weight percent calcium carbonate filler particles and which was biaxially stretched about 400 percent in each direction. The film was commercially available from Exxon Chemical Patents, Inc. under the trade designation EXXAIRE 1500 WVTR. The film defined a thickness of about 0.7 mils, a WVTR of 1553 $g/m^2/24$ hours, and a strength in the machine direction of 1006 grams at an elongation of 30 percent.

The SMS was formed from a meltblown polypropylene layer which had a basis weight of 8.1 gsm and which was positioned between two spunbond polyethylene/polypropylene layers, each of which had a basis weight of 9.5 gsm. The meltblown and spunbond layers were manufactured by Kimberly-Clark. The meltblown layer was composed of up to 5 weight percent polybutylene which was commercially available from Shell under the trade designation DP 8911 and the remainder polypropylene which was commercially available from Exxon under the trade designation 3546G. The spunbond layers were composed of up to 4 weight percent of a 50 percent concentration of titanium dioxide pigment which was commercially available from Ampacet under the trade designation Ampacet 41438. The remainder of the spunbond layers was composed of a 3 weight percent polyethylene/97 weight percent polypropylene copolymer which is commercially available from Shell under the trade designation 6D43. The meltblown layer provided from about 25 to about 35 weight percent of the SMS laminate material. The SMS material defined a WVTR of 4941 $g/m^2/24$ hours and a strength in the machine direction of 5043 grams at an elongation of 30 percent.

The composite backsheet which included the combination of the film and the SMS material defined a WVTR of about 1299 $g/m^2/24$ hours and a strength in the machine direction of 6620 grams at an elongation of 30 percent.

EXAMPLE 2

Material which could be used as the composite backsheet on absorbent articles such as diapers was produced according to the present invention. The liquid impermeable, vapor permeable composite backsheet comprised a low density polyethylene film material having a basis weight of 19.5 grams per square meter which was adhesively attached to a spunbond/meltblown layer (SM) having a basis weight of 20.3 grams per square meter.

The film comprised a biaxially oriented polyethylene film material which included about 50 weight percent calcium carbonate filler particles and which was biaxially stretched about 400 percent in each direction. The film was commercially available from Exxon Chemical Patents, Inc. under the trade designation EXXAIRE 1500 WVTR. The film defined a thickness of about 0.7 mils, a WVTR of 1553 $g/m^2/24$ hours, and a strength in the machine direction of 1006 grams at an elongation of 30 percent.

The SM layer was composed of a meltblown layer having a basis weight of 8.1 gsm and a spunbond layer having a basis weight of 12.2 gsm. The meltblown layer was composed of up to 5 weight percent polybutylene which was commercially available from Shell under the trade designation DP 8911 and the remainder polypropylene which was commercially available from Exxon under the trade designation 3546G. The spunbond layer was composed of up to 4 weight percent of a 50 percent concentration of titanium dioxide pigment which was commercially available from Ampacet under the trade designation Ampacet 41438. The remainder of the spunbond layer was composed of a 3 weight percent polyethylene/97 weight percent polypropylene copolymer which is commercially available from Shell under the trade designation 6D43. The spunbond/meltblown layer defined a WVTR of 4896 $g/m^2/24$ hours and a strength in the machine direction of 3629 grams at an elongation of 30 percent.

The combination of the film and the spunbond/meltblown material defined a WVTR of 1250 $g/m^2/24$ hours and a strength in the machine direction of 4745 grams at an elongation of 30 percent.

COMPARATIVE EXAMPLE 1

Material which could be used as a composite backsheet on absorbent articles such as diapers was produced. The composite backsheet comprised a low density polyethylene film material having a basis weight of about 19.5 grams per square meter which was adhesively attached to a spunbond material having a basis weight of 20.3 grams per square meter.

The film comprised a biaxially oriented polyethylene film material which included about 50 weight percent calcium carbonate filler particles and which was biaxially stretched about 400 percent in each direction. The film was commercially available from Exxon Chemical Patents, Inc. under the trade designation EXXAIRE 1500 WVTR. The film defined a thickness of about 0.7 mils, a WVTR of 1553 $g/m^2/24$ hours, and a strength in the machine direction of 1006 grams at an elongation of 30 percent.

The spunbond layer was composed of up to 4 weight percent of a 50 percent concentration of titanium dioxide pigment which was commercially available from Ampacet under the trade designation Ampacet 41438. The remainder of the spunbond layer was composed of a 3 weight percent polyethylene/97 weight percent polypropylene copolymer which is commercially available from Shell under the trade designation 6D43. The spunbond layer defined a WVTR of 12,306 $g/m^2/24$ hours and a strength in the machine direction of 2701 grams at an elongation of 30 percent.

The combination of the film and the spunbond material defined a WVTR of 1312 $g/m^2/24$ hours and a strength in the machine direction of 2701 grams at an elongation of 30 percent.

The examples representatively illustrate that adding a spunbond/meltblown or spunbond/meltblown/spunbond laminates to a low basis weight breathable film effectively increases the strength of the film while not adversely affecting the breathability of the film. The comparative example also illustrates that not all nonwoven materials provide the strength to the film which is needed to resist tears during use as a disposable absorbent article such as a diaper. Thus, the combination of nonwoven laminates with a low basis weight film can be used to provide a vapor permeable, liquid impermeable composite which has sufficient strength at a cost which allows its use in disposable products.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

We claim:

1. An absorbent article which includes an absorbent and a substantially liquid impermeable, vapor permeable composite backsheet which comprises:
   a) a substantially liquid impermeable, vapor permeable film which defines a basis weight of less than about 20.0 grams per square meter; and
   b) a nonwoven facing layer which is attached to a garment facing surface of said film and which defines a strength in a machine direction of at least about 3000 grams at an elongation of 30 percent.

2. An absorbent article according to claim 1 wherein said basis weight of said film is less than about 15.0 grams per square meter.

3. An absorbent article according to claim 1 wherein said basis weight of said film is less than about 12.0 grams per square meter.

4. An absorbent article according to claim 1 wherein said film defines a water vapor transmission rate of at least about 500 g/sq.m/24 hr as determined according to a Water Vapor Transmission Rate test set forth herein.

5. An absorbent article according to claim 1 wherein said film defines a hydrohead value of at least about 50 centimeters as determined according to a Hydrostatic Pressure Test set forth herein.

6. An absorbent article according to claim 1 wherein said film is a polyolefin film which defines a thickness of less than about 0.025 millimeters.

7. An absorbent article according to claim 1 wherein said film is a linear low density polyethylene film.

8. An absorbent article according to claim 1 wherein said film includes at least about 20 weight percent filler particles.

9. An absorbent article according to claim 8 wherein said filler particles include calcium carbonate.

10. An absorbent article according to claim 8 wherein said film has been stretched in the machine direction at least about 150 percent to cause fractures to form where said filler particles are located.

11. An absorbent article according to claim 8 wherein said film has been biaxially stretched at least about 150 percent in the machine direction and a transverse direction to cause fractures to form where said filler particles are located.

12. An absorbent article according to claim 1 wherein said strength of said nonwoven facing layer in the machine direction is at least about 4000 grams at an elongation of 30 percent.

13. An absorbent article according to claim 1 wherein said nonwoven facing layer defines a basis weight of less than about 30.0 grams per square meter.

14. An absorbent article according to claim 1 wherein said nonwoven facing layer defines a water vapor transmission rate of at least about 2500 g/sq.m/24 hr as determined according to a Water Vapor Transmission Rate test set forth herein.

15. An absorbent article according to claim 1 wherein said nonwoven facing layer defines a hydrohead value of at least about 50 centimeters as determined according to a Hydrostatic Pressure Test set forth herein.

16. An absorbent article according to claim 1 wherein said nonwoven facing layer is a spunbond/meltblown laminate.

17. An absorbent article according to claim 1 wherein said nonwoven facing layer is a spunbond/meltblown/spunbond laminate.

18. An absorbent article according to claim 1 wherein said nonwoven facing layer is adhesively laminated to said film to provide said composite backsheet.

19. An absorbent article according to claim 1 wherein said composite backsheet defines a water vapor transmission rate of at least about 500 g/sq.m/24 hr as determined according to a Water Vapor Transmission Rate test set forth herein.

20. An absorbent article according to claim 1 wherein a ratio of a strength of said composite backsheet to a strength of said film in the machine direction at an elongation of 30 percent is at least about 2:1.

21. An absorbent article which comprises:
   a) a substantially liquid impermeable composite backsheet which includes a polymeric film which defines a basis weight of less than about 20.0 grams per square meter and a nonwoven facing layer attached to a garment facing surface of said film, wherein said composite backsheet defines a water vapor transmission rate of at least about 500 g/sq.m/24 hr as determined according to a Water Vapor Transmission Rate test set forth herein and a hydrohead value of at least about 50 centimeters as determined according to a Hydrostatic Pressure Test set forth herein;
   b) a liquid permeable topsheet which is positioned in facing relation with said composite backsheet; and
   c) an absorbent body located between said composite backsheet and said topsheet.

22. An absorbent article according to claim 21 wherein said hydrohead value of said composite backsheet is at least about 70 centimeters as determined according to said Hydrostatic Pressure Test.

23. An absorbent article according to claim 21 wherein said water vapor transmission rate of said composite backsheet is from about 1000 to about 3000 g/sq.m/24 hr as determined according to said Water Vapor Transmission Rate test.

24. An absorbent article according to claim 21 wherein a ratio of a strength of said composite backsheet to a strength of said film in a machine direction at an elongation of 30 percent is at least about 2:1.

25. An absorbent article according to claim 21 wherein a ratio of a strength of said composite backsheet to a strength of said film in a machine direction at an elongation of 30 percent is at least about 3:1.

26. An absorbent article according to claim 21 wherein said film is substantially coextensive with said nonwoven facing layer.

27. An absorbent article according to claim 21 wherein said film defines a width which is less than a width of said nonwoven facing layer.

28. An absorbent article according to claim 27 wherein said film defines an area which is at least about 70 percent of an area of said nonwoven facing layer.

29. An absorbent article according to claim 27 wherein said film substantially covers a garment side of said absorbent body.

30. An absorbent article which includes an absorbent and a substantially liquid impermeable, vapor permeable composite backsheet which comprises:
   a) a substantially liquid impermeable, vapor permeable polyethylene film which includes at least about 20 weight percent filler particles and which defines a basis weight of less than about 20.0 grams per square meter; and
   b) a meltblown facing layer which is attached in facing relation to a garment facing surface of said film and which defines basis weight of less than about 30.0 grams per square meter and a hydrohead value of at least about 50 centimeters as determined according to a Hydrostatic Pressure Test set forth herein; wherein a ratio of a strength of said composite backsheet to a strength of said film in a machine direction at an elongation of 30 percent is at least about 2:1.

31. An absorbent article according to claim 30 wherein said basis weight of said of polyethylene film is less than about 15.0 grams per square meter.

32. An absorbent article according to claim 30 wherein said basis weight of said polyethylene film is less than about 12.0 grams per square meter.

33. An absorbent article according to claim 30 wherein said polyethylene film includes at least about 30 weight percent of said filler particles.

34. An absorbent article according to claim 30 wherein said polyethylene film is a linear low density polyethylene film.

35. An absorbent article according to claim 30 wherein said polyethylene film defines a thickness of less than about 0.025 millimeters.

36. An absorbent article according to claim 30 wherein said polyethylene film defines a water vapor transmission rate of at least about 500 g/sq.m/24 hr as determined according to a Water Vapor Transmission Rate test set forth herein.

37. An absorbent article according to claim 30 wherein said polyethylene film has been stretched at least about 150 percent in at least one direction to cause fractures to form where said filler particles are located.

38. An absorbent article according to claim 30 wherein said polyethylene film has been biaxially stretched in the machine direction and a transverse direction at least about 150 percent.

39. An absorbent article according to claim 30 wherein said meltblown facing layer comprises polypropylene fibers.

40. An absorbent article according to claim 30 wherein said meltblown facing layer is a spunbond/meltblown laminate.

41. An absorbent article according to claim 30 wherein said meltblown facing layer is a spunbond/meltblown/spunbond laminate.

42. An absorbent article according to claim 30 wherein said hydrohead value of said meltblown facing layer is at least about 50 centimeters as determined according to said Hydrostatic Pressure Test.

43. An absorbent article according to claim 30 wherein said basis weight of said meltblown facing layer is less than about 25.0 grams per square meter.

44. An absorbent article according to claim 30 wherein said composite backsheet defines a water vapor transmission rate of at least about 500 g/sq.m/24 hr as determined according to a Water Vapor Transmission Rate test set forth herein.

45. An absorbent article according to claim 30 wherein said composite backsheet defines a hydrohead value of at least about 70 centimeters as determined according to said Hydrostatic Pressure Test.

46. An absorbent article according to claim 30 wherein said composite backsheet defines a strength in the machine direction of at least about 3500 grams at an elongation of 30 percent.

47. An absorbent article according to claim 30 wherein said ratio of the strength of said composite backsheet to the strength of said polyethylene film in the machine direction at an elongation of 30 percent is at least about 3:1.

* * * * *